(12) United States Patent
Arabi

(10) Patent No.: US 11,862,295 B1
(45) Date of Patent: Jan. 2, 2024

(54) METHOD OF CLASSIFYING CONFORMERS

(71) Applicant: UNITED ARAB EMIRATES UNIVERSTIY, Al Ain (AE)

(72) Inventor: Alya A. Arabi, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/983,075

(22) Filed: Nov. 8, 2022

(51) Int. Cl.
*G16B 15/30* (2019.01)
*G16C 20/50* (2019.01)
*G16C 10/00* (2019.01)

(52) U.S. Cl.
CPC ............ *G16B 15/30* (2019.02); *G16C 10/00* (2019.02); *G16C 20/50* (2019.02)

(58) Field of Classification Search
CPC ........ G16B 15/30; G16B 15/00; G16C 20/50; G16C 20/30; G16C 10/00; G16C 20/70; A61K 48/0066; G06N 10/00; G06N 20/00; G06N 3/08; G06N 3/088; G06N 7/01; G06N 10/20; G06N 10/60; G06N 10/40; G06N 10/80; G06N 10/70; G06N 3/02
USPC ...... 702/1, 19, 22–23, 27, 30, 127; 703/2, 6, 703/11–12
See application file for complete search history.

(56) References Cited

U.S. PATENT DOCUMENTS

| 7,904,283 B2 | 3/2011 | Merz, Jr. et al. |
| 10,626,154 B2 | 4/2020 | Steyaert et al. |
| 2003/0228630 A1* | 12/2003 | Tsuda ..................... G16B 15/00 435/7.1 |
| 2005/0170385 A1* | 8/2005 | Carlson ................ C12Q 1/6804 702/19 |
| 2022/0068439 A1* | 3/2022 | Yamazaki .............. G06N 10/00 |

FOREIGN PATENT DOCUMENTS

WO  WO-2014033670 A2 *  3/2014  .......... G06F 19/704

OTHER PUBLICATIONS

Chidangil et al., "A molecular electrostatic potential mapping study of some fluoroquinolone anti-bacterial agents," Molecular Modeling Annual, Aug. 4, 1998, 250-258.
Kahn, "Molecular Electron Density Surface," Department of Chemistry and Biochemistry, UC Santa Barbara, ® 2005-2012.

(Continued)

*Primary Examiner* — Jeffrey P Aiello
(74) *Attorney, Agent, or Firm* — Nath, Goldberg & Meyer; Richard C. Litman

(57) ABSTRACT

A system and method for classifying conformers of a molecule are provided. The methods for classifying conformers of a molecule include selecting a target molecule, generating a list of conformers of the target molecule, completing a quantum mechanics (QM) simulation for each conformer, extracting an electronic energy for each conformer from the corresponding QM simulation, calculating average electron density (AED) values corresponding to a most electronegative group of the target molecule, generating a plot of the electronic energies vs. the calculated AED values, and classifying conformers based on this plot. Similar methods can also be used to predict shapes of electrostatic potential (ESP) maps for conformers of a molecule. These ESP maps can, in turn, be used to identify conformers of the molecule having desired chemical or pharmaceutical properties.

20 Claims, 2 Drawing Sheets

(56) References Cited

OTHER PUBLICATIONS

Ferro Costas et al., "A QTAIM-based energy partitioning for understanding the physical origin of conformational preferences: application to the Z effect in O=C-X-R and related units," Journal of Computational Chemistry, vol. 33, Issue 32, Dec. 15, 2012.

Matta et al., "The bioisosteric similarity of the tetrazole and carboxylate anions: clues from the topologies of the electrostatic potential and of the electron density," European Journal of Medicinal Chemistry, vol. 45, Issue 5, May 2010, pp. 1868-1872.

Matta et al., "Electron Density Descriptors as Predictors in Quantitative Structure-to-Activity/Property-Relationships (QSAR/QSPR)," Future Medicinal Chemistry, vol. 3, No. 8, Jun. 27, 2011.

Arabi et al., "Electrostatic Potentials and Average Electron Densities of Bioisosteres in Methylsquarate and Acetic Acid," Future Medicinal Chemistry, vol. 8, No. 4, Mar. 15, 2016.

Arabi, "Route to Drug Design via Bioisosterism of Carboxyl and Sulfonamide Groups," Future Medicinal Chemistry, vol. 9, No. 18, Nov. 9, 2017.

Arabi, "Quantitative Evaluation of Bioisosteres in Drug Design," CBMC19 CompBioMed Conference 2019, Institute of Engineering and Technology, Savoy Place London, UK, Sep. 25-27, 2019.

Arabi, "Atomic and molecular properties of nonclassical bioisosteric replacements of the carboxylic acid group," Future Medicinal Chemistry, vol. 12, No. 12, May 13, 2020.

Faramarzi et al., "NBO and QTAIM Investigations of the conformers of 1, 4-dioxane-2, 3-bis(pyridin-1-ium) and 1, 4-dioxane-2, 5-bis(pyridin-1-ium) molecules," Eurasian Chemical Communications, (2020).

Setianto, et al., "Visualization the electrostatic potential energy map of graphene quantum dots," AIP Conference Proceedings, vol. 2219, No. 1, AIP Publishing LLC, Jan. 19, 2021.

Arabi, "Artificial Intelligence in Drug Design: Algorithms, Applications, Challenges and Ethics," Future Drug Discovery, vol. 3, No. 2, Apr. 29, 2021.

Duarte et al., "A New Synthetic Route and Comprehensive Topological Study of a Benzimidazole Derivative," Journal of the Brazilian Chemical Society, 33 (3), Mar. 2022.

\* cited by examiner

METHOD OF CLASSIFYING CONFORMERS

BACKGROUND

1. Field

The disclosure of the present patent application relates to methods and systems for classifying conformers of a molecule to aid in many applications including but not limited to the development of drug design, to assist in determining chemical reactivities, to resolve materials science issues, or for other purposes.

2. Description of the Related Art

In general, various chemical and other physical properties of various molecules can be classified by numerous tools. For example, methods of using electron density to quantify the mean positions of atoms in chemical compounds, their chemical bonds, and other information are currently generally known.

For example, U.S. Pat. No. 10,626,154 discloses that x-ray crystallography can be used to generate a three-dimensional picture of the density of electrons within a molecule. This electron density can then be used to determine the mean positions of the atoms in the molecule, their chemical bonds, their disorder, and various other information.

Similarly, U.S. Pat. No. 7,904,283 discloses various computational methods for designing a drug by predicting free energy binding. Among the types of free energy binding used is entropic free energy, which comprises a conformational entropy component, calculated using a quantum mechanical Hamiltonian and/or a quantum mechanical/molecular mechanical approach.

Drug design development, for example, has many challenges, as small differences in a drug molecule's structure can significantly affect its biological activity. One particularly useful tool to meet these challenges is the investigation, identification, classification, and analysis of various conformers of a molecule. Chemical conformers are chemical compounds that have the same molecular formula but a different rotation from one another at one bond in the molecule. Chemical conformers are also known as conformational isomers.

However, there are no currently known tools capable of suitably analyzing and classifying chemical conformers of a given molecule. At best, it is possible to look, e.g., at the energy levels of various conformers, yet it is not currently possible to transfer such knowledge to other molecules to aid in the development of new drug design, to assist in determining chemical reactivities, to resolve materials science issues, or for other purposes. Thus, a new tool solving these problems is desired.

SUMMARY

The methods and systems described herein relate to the identification and classification of various conformers of a molecule. More specifically, the present methods and systems relate to a new use of the Average Electron Density (AED) tool, a qualitative tool to assist in developing and classifying conformers of a molecule of interest, and the topology of their electrostatic potential (ESP) maps. The present methods and systems can then be used to aid in the development of drug design and many other applications including, but not limited to, materials science applications, the development of chemical probes, determining chemical reactivities, conducting analyses of crystalline structures, and computational chemistry applications.

In one embodiment, the present subject matter relates to a method for classifying conformers of a molecule, the method comprising: selecting a target molecule of interest; generating a list of conformers of the target molecule of interest; completing a quantum mechanics (QM) simulation for each conformer in the list of conformers; extracting an electronic energy for each conformer from the corresponding QM simulation; calculating average electron density (AED) values corresponding to a most electronegative group of the target molecule of interest; generating a plot of the electronic energies of each conformer vs. the calculated AED values; and classifying each conformer in the list of conformers based on the plot of the electronic energies vs. the calculated AED values.

In another embodiment, the present subject matter relates to a method for classifying conformers of a molecule, the method comprising: selecting a target molecule of interest; generating a list of conformers of the target molecule of interest; completing a quantum mechanics (QM) simulation for each conformer in the list of conformers; extracting an electronic energy for each conformer from the corresponding QM simulation; calculating average electron density (AED) values corresponding to a most electronegative group of the target molecule of interest; generating a plot of the electronic energies of each conformer vs. the calculated average electron density (AED) values; generating electrostatic potential (ESP) maps for each conformer of the target molecule of interest; positioning the generated ESP maps such that a most electronegative group of the target molecule of interest is kept constant in one spot, based on the calculated AED values corresponding to the most electronegative group of the target molecule of interest, to facilitate a visual comparison of the electrostatic potential (ESP) maps; and classifying each conformer based on the average electron densities (AED) and energies; the conformers of one group share the same topology of the electrostatic potential (ESP) maps.

In a further embodiment, the presently claimed subject matter relates to a method for predicting shapes of electrostatic potential (ESP) maps for conformers of a molecule, the method comprising: selecting a target molecule of interest; generating a list of conformers of the target molecule of interest; completing a quantum mechanics (QM) simulation for each conformer in the list of conformers; extracting an electronic energy for each conformer from the corresponding QM simulation; calculating average electron density (AED) values corresponding to a most electronegative group of the target molecule of interest; generating a plot of the electronic energies of each conformer vs. the calculated average electron density (AED) values; classifying each conformer in the list of conformers based on the plot of the electronic energies vs. the calculated AED values; and predicting shapes of electrostatic potential (ESP) maps for conformers based on the classification of each conformer.

In certain embodiments, the calculated average electron densities (AED) values can be calculated as a sum of electron population divided by a sum of volumes, of all atoms. In other embodiments, the average electron density (AED) values can be used to predict shapes of electrostatic potential (ESP) maps for conformers.

In a further embodiment, the present subject matter relates to a method for identifying conformers of a molecule having desired chemical or pharmaceutical properties, the method comprising: predicting shapes of electrostatic potential (ESP) maps for conformers of the molecule according to the herein described methods; identifying the conformers of the molecule having the desired chemical or pharmaceutical properties; and selecting the identified conformers of the molecule for further analysis. In particular non-limiting example, the step of identifying the conformers of the molecule having the desired chemical or pharmaceutical properties comprises screening the conformers of the molecule for a desired shape. This desired shape permits the conformer of the molecule to bind to an active site of a receptor of interest or to react with other molecules. This is important as the shapes of different conformers can cause the various conformers to have different interactions with a given protein in drug design, and for some conformers to be able to bind to a receptor of interest, while others cannot. Likewise, different conformers of a molecule may have an impact on the chemical reactivities of the molecule, as depending on the ESP topology of a specific conformer, the molecule may be blocked from desired chemical reactions. Accordingly, studying the conformers of a molecule may help predict the reactivity of that molecule. Similarly, conformers of the molecules having the desired shape would be expected to share similar material properties.

In this regard, such methods may further comprise screening the conformers of the molecule for the desired chemical properties, pharmaceutical properties, or chemical and pharmaceutical properties. For example, in addition to the example of the different conformer shapes noted above, the desired pharmaceutical properties may be one or more selected from the group consisting of potency, solubility, permeability, metabolic stability, transporter effects, bioavailability, metabolism, clearance, and toxicity. Similarly, in addition to the example of the different conformer shapes noted above, the desired chemical properties may be one or more selected from the group consisting of mechanical, electrical, thermal, magnetic, optical, and deteriorative properties which may impact surface chemistry as it relates to materials sciences, for example. Impacts on engineering applications are also possible, for the reasons given above.

These and other features of the present subject matter will become readily apparent upon further review of the following specification.

DETAILED DESCRIPTION OF THE PREFERRED EMBODIMENTS

Figure 1:
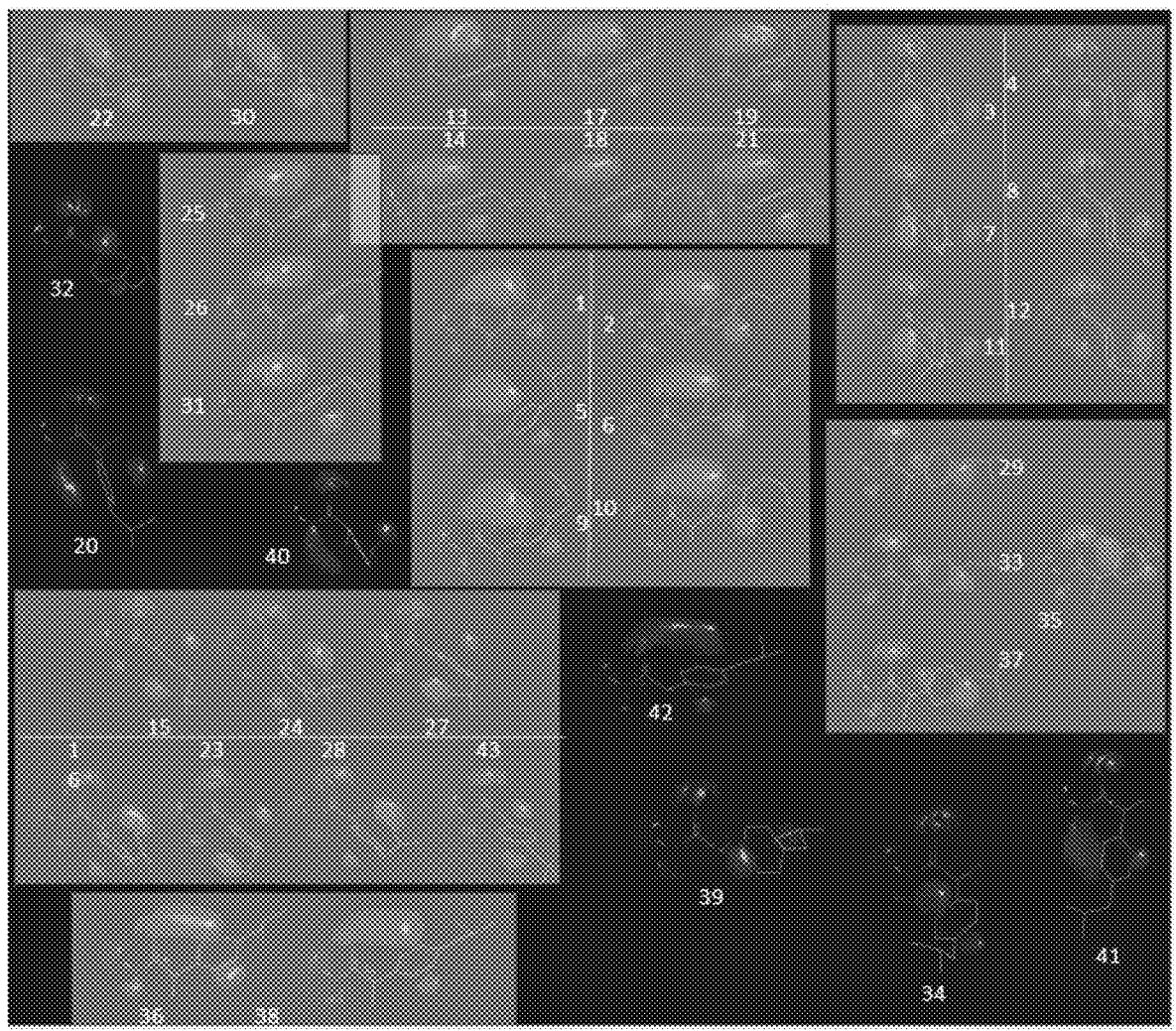
FIG. 1 shows exemplary ESP maps for conformers of the molecule ibuprofen, with each identified conformer of ibuprofen separately numbered.

The presently described subject matter relate to the identification and classification of various conformers of a molecule. More specifically, the present methods and systems relate to a new use of the Average Electron Density (AED) tool to assist in developing and classifying conformers of a molecule of interest and positioning their electrostatic potential (ESP) maps. The activity of a molecule is linked to its chemical structure. Therefore, studying this structure is extremely important. Once the chemical conformers of a molecule are classified, further studies can be done to determine how the conformers may impact drug design, chemical reactivities, engineering applications, and materials science applications.

In one embodiment, the present subject matter relates to a method for classifying conformers of a molecule, the method comprising: selecting a target molecule of interest; generating a list of conformers of the target molecule of interest; completing a quantum mechanics (QM) simulation for each conformer in the list of conformers; extracting an electronic energy for each conformer from each corresponding QM simulation; calculating average electron density (AED) values corresponding to a most electronegative group of the target molecule of interest; generating a plot of the electronic energies of each conformer vs. the calculated AED values; and classifying each conformer in the list of conformers based on the plot of the electronic energies vs. the calculated AED values.

This approach permits the translation of pictures and conformers to numbers using quantum methods. Previously, it was possible to evaluate and classify conformers based on, for example, their coordinates. The present tool represents a new highly accurate and specific quantitative method for evaluating, measuring, classifying, and working with conformers.

List of Conformers

The list of conformers for a specific molecule can be generated using any specific software package known to one of ordinary skill in the art. For example, the list of conformers for ibuprofen (43 conformers) can be generated using Omega from the OpenEye Scientific software package, owned by Cadence Molecular Sciences (Santa Fe, NM). Omega is used to generate multi-conformer structure databases with high speed and reliability. Omega conformational databases can be used as input to various applications, including shape comparison tools.

Other alternative software packages are available as well for generating the list of conformers. One such alternative software package is the Spartan software, owned by Wavefunction, Inc. (Irvine, CA).

Quantum Mechanics (QM) Simulation

Once the list of conformers for a particular molecule has been generated, a quantum mechanics (QM) simulation can be performed on the various identified conformers. In one embodiment, the electronic energy, $E_e[\rho(r)]$, to be extracted for each conformer from the corresponding QM simulation can be written as a function of the electron density:

$$E_e[\rho(r)] = T[\rho(r)] + V_{en}[\rho(r)] + J[\rho(r)] + Q[\rho(r)] \quad (1)$$

where $T[\rho(r)]$ is the kinetic energy of the electrons, $V_{en}[\rho(r)]$ is the nuclear-electron attraction energy, $J[\rho(r)]$ is the classical electron-electron repulsion energy, and $Q[\rho(r)]$ is the non-classical (quantum) electron-electron interaction energy. The second and third terms in Equation (1) are known and can be computed according to Equations (2) and (3), respectively:

$$V_{en}[\rho(r)] = -\sum_{A=1}^{M} \int \frac{Z_A}{|r - R_A|} \rho(r) dr \quad (2)$$

$$J[\rho(r)] = \frac{1}{2} \int \int \frac{\rho(r_1)\rho(r_2)}{r_{12}} dr_1 dr_2 \quad (3)$$

Since the non-interacting kinetic energy (Equation (5)) is not equal to $T[\rho(r)]$, the difference between these two terms is combined with $Q[\rho(r)]$ to define the exchange-correlation energy, $E_{xc}[\rho(r)]$:

$$T_s[\{\phi_i\}] = -\frac{1}{2}\sum_{i=1}^{n}\int \phi_i^*(r)\nabla^2\phi_i(r)dr \quad (5)$$

$$E_{xc}[\rho(r)] = T[\rho(r)] - T_s[\{\phi_i\}] + Q[\rho(r)] \quad (6)$$

The only unknown term here is the exchange-correlation functional. The B3LYP functional is used as the exchange-correlation functional.

The B3LYP functional is a global hybrid (GH) functional that takes the form given in Equation (7) and can be theoretically justified with the adiabatic connection formula:

$$E_{xc}^{GH} = c_x E_x^{HF} + (1-c_x)E_x^{DFT} + E_c^{DFT} \quad (7)$$

In one embodiment, the quantum mechanics (QM) simulation can be performed using Gaussian® software, for example, Gaussian 16, available from Gaussian, Inc. (Wallingford, CT), which is an electronic-structure modeling software that facilitates quantum chemistry calculations. Other QM software, such as Q-Chem (available from Q-Chem, Inc., Pleasanton, CA), The General Atomic and Molecular Electronic Structure System (GAMESS, maintained by members of the Gordon Research Group at Iowa State University, Ames, IA), or MolPro (available from the University of Stuttgart, Stuttgart, Germany) could be used. This QM analysis will obtain a wavefunction file from which the various properties of each conformer can be extracted. Therefore, the Gaussian 16 software is capable of completing a quantum mechanics (QM) simulation for each conformer in the list of conformers, extracting an electronic energy for each conformer from the corresponding QM simulation, and generating the wavefunction from which volumes and electron densities will be extracted after the QTAIM analysis.

In drug design, for example, it is important to rationally design molecules with a good shape complementarity to the appropriate receptor. The shape of a molecule can be determined uniquely given the unique electron correlations and the Pauli exclusion principle which prohibits two electrons of any molecule to have the same four electronic quantum numbers. However, the quantum mechanics is a probabilistic theory, and the electron density falls off roughly exponentially with the distance from the nucleus, and the repulsive energy grows roughly exponentially as the distance between two nuclei decreases. In typical molecules, the increase is so rapid that one molecule cannot penetrate a region just about half an angstrom beyond the point of minimum interaction. The electron density depends on the atomic composition and the chemical connectivity of atoms in the molecule. One way to determine molecular shape is to calculate the electron density and display the region where the electron density is larger than some cut-off value as a three-dimensional surface. Such calculations necessitate a quantum chemical approach and are possible with any molecule.

Average Electron Density (AED)

The average electron density (AED) tool is based on the partitioning of a molecule into atomic basins using the quantum theory of atoms in molecules (QTAIM) partitioning scheme. The average electron density (AED) is defined as the total electron population of a group of a molecule or of the full molecule divided by the corresponding volume. The internal interatomic limits between two atoms are determined by the internal zero-flux interatomic surfaces within the molecular interior, and the outer limit is set at the external 0.001 atomic unit isodensity envelope. The volumes and electron populations used to calculate the AED are those defined within Bader's quantum theory of atoms in molecules, a theory that partitions the molecular electron density into separate atomic basins separated by surfaces of zero-flux in the gradient vector field associated with the density. The atomic properties are then obtained by numerical integrations over each atomic basin. The AED properties of a specific molecular group are the sum of the properties of the atoms constituting this group.

The average electron density of a group is given by the formula:

$$\rho = \Sigma N i / \Sigma V i \quad (8)$$

where Ni is the electron population of each atom i, and Vi is the volume of each atom i.

In one embodiment, the wavefunction file obtained from the QM simulation can be further analyzed and processed using AIMAll software, from TK Gristmill Software (Overland Park, KS), based on the QTAIM theory. The AIMAll software package can be used for atomic integrations based on QTAIM. The interatomic basins can be delimited by zero-flux surfaces, and the outer limit of the atomic basins can be defined at three different isodensity envelopes of 0.0004, 0.001, and 0.002 a.u. AIMAll software is typically used for performing quantitative and visual QTAIM analyses of molecular systems, starting from molecular wavefunction data.

Likewise, AED values can be calculated by starting with, for example, a Gaussian software package, such as, for example, Gaussian16, with molecules optimized in the gas phase. In one embodiment, the level of theory used is the B3LYP density functional theory, namely B3LYP/6-311++G(d,p)//B3LYP/6-311++G(d,p) with ultrafine pruned (99, 590) grids and 'tight' self-consistent field optimization criteria. Vibrational frequency analysis was completed to confirm that the optimized geometries have no imaginary frequencies, in other words, they are not transition states. Here even if other (reasonable) details of the QM simulation are used, they will still give the same result.

In another embodiment, the Hershfield scheme may be used for partitioning the basins of atoms in molecules. The Hirshfeld (1977) method apportions the electron density among the atoms by the appropriate weighting. The weights are related by the atomic contribution to the promolecular density:

$$w_A(r) = \frac{\rho_{atm}^A(r)}{\rho_{pro}(r)}$$

The fragment of the density apportioned to atom A is $$\rho_{frag}^A(r) = w_A(r)\rho_{mol}(r)$$

An alternative scheme is based on the atomic contributions to the total promolecular potential $V_{pro}$ defined as the sum of the electronic and nuclear contributions.

In one embodiment of the present methods, AED values are determined for only a most electronegative group of the molecule being studied. For example, in the study of the conformers of ibuprofen, the AED values for the COOH group, being the most electronegative group of the molecule, were used for further analysis. In another embodiment, AED values are determined for the entire molecule being studied.

Once the AED values are generated, the same software package can be used to generate a plot of the electronic energies of each conformer vs. the calculated AED values.

Figure 2:
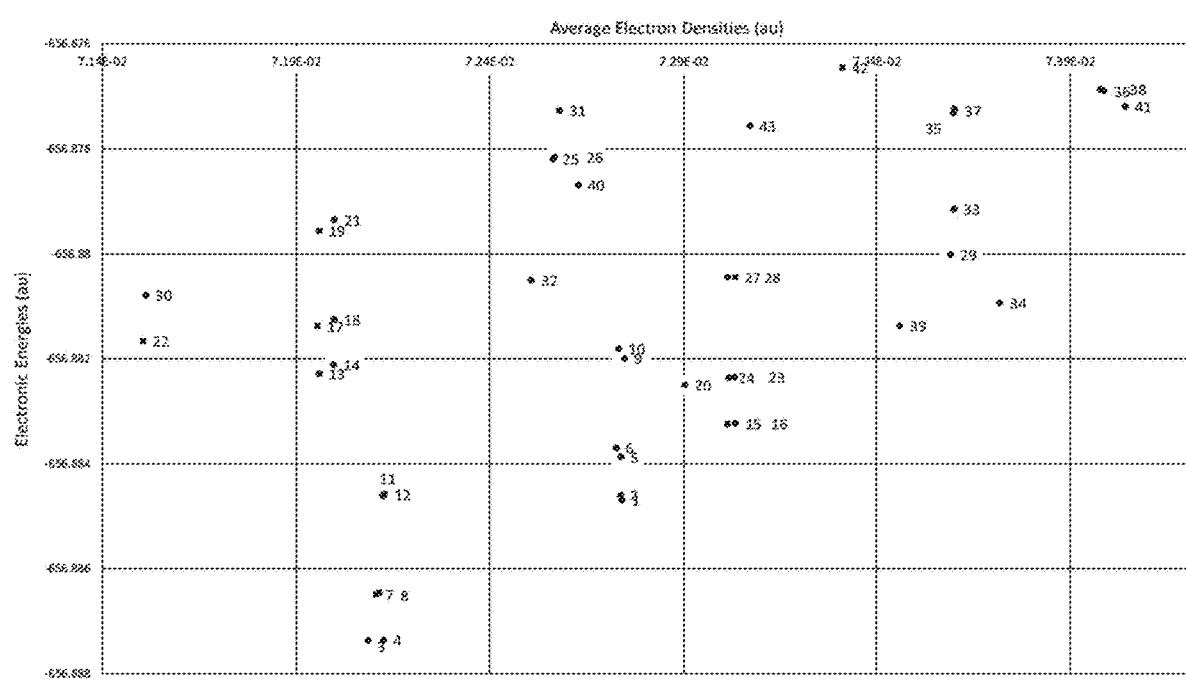
FIG. 2 shows a plot of electronic energies vs. AEDs for conformers of the molecule ibuprofen.

Each conformer can then be classified based on this plot of the electronic energies of each conformer vs. the calculated AED values. By way of non-limiting example, FIG. 2 shows a plot of electronic energies vs. AEDs for the conformers of the molecule ibuprofen. A review of FIG. 2 shows how conformers are classified in groups of conformers under each other (i.e., those conformers sharing the same AED value are classified one under the other). The label by each point in FIG. 2 represents the number of the conformer.

Electrostatic Potential Maps (ESPs)

Molecular ESPs were first introduced in the 1970s, and they are ubiquitously used for the identification of electrophilic and nucleophilic sites for predicting reactivities and gaining more insight about the directions of interactions, and thus mechanisms of various processes. Molecular electrostatic potentials are typically calculated from a molecule's charge density (the continuous electron density and the discrete nuclear charge distribution) and can be used to identify the reactive regions of a molecule.

The molecular ESP, V(r), is obtained at the quantum level by the following formula:

$$V(r) = \sum_A \frac{Z(A)}{|R(A) - r|} - \int \frac{\rho(r')}{|r' - r|} dr' \qquad (9)$$

where Z(A) is the atomic number, R(A) is the position vector of nucleus A, r is the position vector of the point at which V(r) is evaluated and ρ(r') is the electron density at a position vector r'. The results of the equation are in atomic units, with the electronic charge taken as unity.

Various software packages offer three ways to evaluate the electrostatic potential. First, the true electrostatic potential can be calculated based on molecular orbital data. This is rather time consuming, especially if large Gaussian basis sets were used to form molecular orbitals but should give the best representation of the electrostatic potential. Second, fitting of the electrostatic potential can be performed based on the quantum-chemically derived multipole moments of the molecule. In other words, the software tries to determine what kind of potential would best reproduce the dipole and octupole moment of the molecule. Third, the electrostatic potential can be calculated based on partial atomic charges.

ESP maps are typically limited to qualitative comparisons. However, by combining the use of ESP maps for a conformer with the calculation of average electron density (AED) values and of electronic energies for each conformer using a quantum mechanics (QM) simulation, it is now possible to quantitatively determine similarities and differences between different conformers of a molecule. That is, the present subject matter is directed to use of the AED value of a molecule to classify or categorize the shapes of the electrostatic potential maps of conformers. In one embodiment, the AED value of the most electronegative group of the molecule being studied is used to classify the shapes of the electrostatic potential maps of conformers. That is, the AED value can be used herein to categorize the ESP maps of various conformers of a molecule depending on their shapes. In this regard, one embodiment of the present subject matter contemplates positioning the already generated ESP maps such that a most electronegative group of the target molecule of interest is kept constant in one spot, based on the calculated AED values corresponding to the most electronegative group of the target molecule of interest, to facilitate a visual comparison of the electrostatic potential (ESP) maps.

ESP maps can be plotted using a variety of software packages presently available to those of ordinary skill in the art. By way of non-limiting example, the subunit Vida from the OpenEye Scientific software package, owned by Cadence Molecular Sciences (Santa Fe, NM), can be used to plot ESP maps of a given molecule. Vida is typically used for molecular modeling, as it can present advanced 3D graphics for high quality molecular visualizations. Similarly, the ChemCraft software package can likewise be used to generate ESP maps of a given molecule. ChemCraft is another graphical software package for visualization of quantum chemistry computations, particularly useful with Gaussian software, and is available at https://www.chemcraftprog.com. ChemCraft can render 3D pictures of molecules by atomic coordinates with the possibility to examine or modify any geometrical parameter in the molecule. ChemCraft can be used as a graphical user interface for the GAMESS (Gordon Research Group, Iowa State University) and Gaussian program packages, as can any other QM package.

Many other molecular visualization programs allow display of electrostatic potential maps based on quantum chemical calculations. MOLDEN (available at https://www.theochem.ru.nl/molden) can calculate electron density surfaces and electrostatic potential surfaces based on the information in the output files of Gaussian or Firefly (PC GAMESS) calculations.

According to one embodiment of the present subject matter, once generated, the ESP maps for each of the various conformers of a molecule are displayed/positioned such that the "lobe" of the most electronegative group of the molecule are always in the same position and/or orientation.

To obtain ESP maps, the results of using the above equation on a specific molecule, conformer, etc. are used to generate a figure, or "map", showing the different lobes and features of the specific compound. In this regard, FIG. 1 shows exemplary ESP maps of all 43 conformers identified for the molecule ibuprofen using the procedures as described herein. In FIG. 1, each of the 43 ESP maps are labeled to show which conformer of ibuprofen they correspond to. Further, as can be seen by referring to FIG. 1, each separate ESP map can be readily rotated such that the most electronegative group (in this case for ibuprofen, the —COOH group) is kept constant in one spot to facilitate a visual comparison of the electrostatic potential (ESP) maps In this regard, FIG. 1 shows the ESP maps of the groups of conformers as shown in the energy vs. AED plot in FIG. 2. The negative and positive lobes are in red and blue, respectively. Each group is highlighted in a separate box. The green line separates two subgroups that are very close to each other in FIG. 2. The number by each ESP map is the number of the conformer as used in FIG. 2. The ESP maps of all ibuprofen conformers are displayed with the COOH being consistently to the left with the carbonyl group pointing North (for ease of visual comparison).

Drug Design

Once the present methods are performed to classify the specific conformers of a given molecule, the knowledge can be used to determine which conformers specifically would be best suited for drug design. Conformational changes in a drug molecule can have drastic effects on its efficacy. The changes in conformation can cause a change in the stability (and therefore the half-life) of the molecule, but more importantly they cause a change in the shape of the molecule (and therefore its spatial arrangement), which may block it sterically from binding into the active site of the relevant receptor. Accordingly, the present tool is extremely helpful for determining which conformers of a drug molecule are most likely to bind to the active site of the relevant receptor, thus speeding the drug design process by allowing the focus to be on those conformers most likely to be successful.

The screening process to determine potential drug candidates can be conducted according to any method known to those of ordinary skill in the art such as, for example, using high-throughput screening arrays. The present methods and systems can speed up what is commonly a long and difficult process by targeting specific conformers of the selected molecules that are more likely to possess a desired activity, removing one or more steps from the typical screening process. The present methods and systems act as a filter to enrich the hit rate compared with typical random screening of conformers of a given molecule, but not different molecules, although the latter is also possible.

Materials Science

Once the present methods are performed to classify the specific conformers of a given molecule, the knowledge can be used to determine which conformers specifically would be best suited for satisfying certain materials science needs and requirements. For one example, selecting a building material based on different conformers of the same molecule can lead to different physical properties of the material build, e.g., due to possibly different electron conductivity (melting properties, etc.). Therefore, classifying conformers in groups that share similar ESP maps means moving one step forward in grouping conformers that would likely share similar material properties once used in building materials. This can be seen from Blaskovits et al., "Is a Single Conformer Sufficient to Describe the Reorganization Energy of Amorphous Organic Transport Materials?," *J. Phys. Chem. C* 2021, 125, 31, 17355-17362 (https://pubs.acs.org/doi/10.1021/acs.jpcc.1c04067), the contents of which are hereby incorporated by reference in their entirety.

Chemical Reactivities

Once the present methods are performed to classify the specific conformers of a given molecule, the knowledge can be used to determine which conformers specifically would be best suited for various chemical reactivities. Conformational changes in a molecule can have drastic effects on its ability to react with other molecules. Different conformers have different shapes, i.e., their densities change, and therefore their ESP maps (which is a guide to the most reactive areas of a molecule) change. Thus, classifying conformers in groups that share similar ESP maps means classifying conformers in groups that share similar reactivities. Likewise, depending on the shape of the conformer, it may be sterically blocked from reacting with another molecule. Accordingly, the present tool is extremely helpful for determining which conformers of a molecule are most likely to successfully complete various chemical reactions.

EXAMPLES

Example 1—Procedure for Generating the Electronic Energies Vs. AED Plot (FIG. 2) and the ESP Maps (FIG. 1) for Ibuprofen The following describes the methodology used for generating FIGS. 1 and 2 for ibuprofen:
1. The ibuprofen structure was obtained and its conformers were generated using the Omega2 tool in OpenEye. A total of 43 conformers were generated.
2. The xyz coordinates of each conformer were extracted to build Gaussian input files.
3. Gaussian single point simulations were completed using the B3LYP functional with a triple zeta Pople basis set and ultrafine grids. The electronic energies of all conformers were collected from these simulations.
4. AIMAll analysis was completed on the wavefunction generated from the Gaussian simulations.
5. The volume (v) and electron population (e) in each atom of the most electronegative group (i.e. COOH in this case) was collected from the AIMAll output.
6. $[e(C)+e(O)+e(O)+e(H)]/[v(C)+v(O)+v(O)+v(H)]=$ AED of the COOH.
7. This equation was repeated for the COOH in each of the ibuprofen conformers.
8. A plot of the electronic energies (from the Gaussian calculation) vs. the AED of the COOH in each conformer was generated (FIG. 2). In this plot, the conformers are automatically classified into groups. The ESP map of each group of conformers (FIG. 1) shares almost identical topologies in the distribution of the negative (red) and positive (blue) lobes. Therefore, the conformers within the same group share the same reactivity in chemistry, interaction in drug design, and properties in material sciences, etc.
9. Although some groups of conformers may share lots of similarities with other groups, they still differ in shape, size, or location of either the blue or the red lobes. The AED tool groups the conformers in clusters that share almost identical ESP maps, while differentiating each group from another group even with the subtle differences.

It is to be understood that the methods and systems described herein are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method for identifying conformers of a molecule having desired chemical, material, or pharmaceutical properties, the method comprising:
   predicting shapes of electrostatic potential (ESP) maps for conformers of the molecule according to a method comprising:
      selecting a target molecule of interest;
      generating a list of conformers of the target molecule of interest;
      completing a quantum mechanics (QM) simulation for each conformer in the list of conformers:
      extracting an electronic energy for each conformer from the corresponding QM simulation;
      calculating average electron density (AED) values corresponding to a most electronegative group of the target molecule of interest;
      generating a plot of the electronic energies of each conformer vs. the calculated average electron density (AED) values;
      classifying each conformer in the list of conformers based on the plot of the electronic energies vs. the calculated AED values; and
      predicting shapes of electrostatic potential (ESP) maps for conformers based on the classification of each conformer;
   identifying the conformers of the molecule having the desired chemical, material, or pharmaceutical properties; and
   chemically synthesizing the identified conformers of the molecule.

2. The method of claim 1, wherein the step of identifying the conformers of the molecule having the desired chemical, material, or pharmaceutical properties comprises screening the conformers of the molecule for a desired shape.

3. The method of claim 2, wherein the desired shape permits the identified conformers to bind to an active site of a receptor of interest.

4. The method of claim 2, wherein the conformers having the desired shape share similar material properties.

5. The method of claim 2, wherein the desired shape permits the identified conformers to react with other molecules.

6. The method of claim 2, wherein the identified conformers are further investigated for the desired chemical, material, or pharmaceutical properties.

7. The method of claim 6, wherein the desired chemical, material, or pharmaceutical properties are one or more selected from the group consisting of potency, solubility, permeability, metabolic stability, transporter effects, bioavailability, metabolism, clearance, toxicity, mechanical, electrical, thermal, magnetic, optical, and deteriorative properties which may impact surface chemistry.

8. The method of claim 2, wherein the desired shape permits the identified conformers to have a desired interaction with a given protein.

9. The method of claim 2, wherein the desired shape permits the identified conformers to have a desired chemical reactivity.

10. The method of claim 2, wherein the desired shape permits the identified conformers to have a desired material property.

11. The method of claim 2, wherein the desired shape permits the identified conformers to have a desired biological activity.

12. The method of claim 2, wherein the desired shape permits the identified conformers to have a desired interaction.

13. A method for identifying conformers of a molecule having desired chemical, material, or pharmaceutical properties, the method comprising:
    predicting shapes of electrostatic potential (ESP) maps for conformers of the molecule according to a method comprising:
        selecting a target molecule of interest;
        generating a list of conformers of the target molecule of interest;
        completing a quantum mechanics (QM) simulation for each conformer in the list of conformers;
        extracting an electronic energy for each conformer from the corresponding QM simulation;
        calculating average electron density (AED) values corresponding to a most electronegative group of the target molecule of interest;
        generating a plot of the electronic energies of each conformer vs. the calculated average electron density (AED) values;
        classifying each conformer in the list of conformers based on the plot of the electronic energies vs. the calculated AED values; and
        predicting shapes of electrostatic potential (ESP) maps for conformers based on the classification of each conformer; and
    identifying the conformers of the molecule having the desired chemical, material, or pharmaceutical properties by screening the conformers of the molecule for a desired shape;
    wherein the identified conformers are further investigated for the desired chemical, material, or pharmaceutical properties which are one or more selected from the group consisting of potency, solubility, permeability, metabolic stability, transporter effects, bioavailability, metabolism, clearance, toxicity, mechanical, electrical, thermal, magnetic, optical, and deteriorative properties which may impact surface chemistry.

14. The method of claim 13, wherein the desired shape permits the identified conformers to bind to an active site of a receptor of interest.

15. The method of claim 13, wherein the conformers having the desired shape share similar material properties.

16. The method of claim 13, wherein the desired shape permits the identified conformers to react with other molecules.

17. The method of claim 13, wherein the desired shape permits the identified conformers to have a desired interaction with a given protein.

18. The method of claim 13, wherein the desired shape permits the identified conformers to have a desired chemical reactivity.

19. The method of claim 13, wherein the desired shape permits the identified conformers to have a desired material property.

20. The method of claim 13, wherein the desired shape permits the identified conformers to have a desired biological activity.

* * * * *